United States Patent
Nie et al.

(10) Patent No.: US 10,773,020 B2
(45) Date of Patent: Sep. 15, 2020

(54) INFUSION SITE LEAK DETECTION DEVICE

(71) Applicant: Becton, Dickinson and Company, Franklin Lakes, NJ (US)

(72) Inventors: Weiyan Nie, Winchester, MA (US); Zhixiong Liu, Bedford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 323 days.

(21) Appl. No.: 15/661,127

(22) Filed: Jul. 27, 2017

(65) Prior Publication Data

US 2017/0319781 A1    Nov. 9, 2017

Related U.S. Application Data

(62) Division of application No. 14/045,261, filed on Oct. 3, 2013, now Pat. No. 9,750,876.

(60) Provisional application No. 61/711,285, filed on Oct. 9, 2012.

(51) Int. Cl.
*A61M 5/168* (2006.01)
*A61M 5/158* (2006.01)

(52) U.S. Cl.
CPC ........ *A61M 5/16831* (2013.01); *A61M 5/158* (2013.01); *A61M 2005/1588* (2013.01)

(58) Field of Classification Search
CPC .............. A61M 5/14248; A61M 5/158; A61M 5/16831; A61M 2005/1586; A61M 2005/1587; A61M 2005/1588
See application file for complete search history.

(56) References Cited

U.S. PATENT DOCUMENTS

| | | |
|---|---|---|
| 6,461,329 B1 | 10/2002 | Van Antwerp et al. |
| 6,752,785 B2 | 6/2004 | Van Antwerp et al. |
| 2003/0009131 A1 | 1/2003 | Van Antwerp et al. |
| 2011/0184342 A1 | 7/2011 | Pesach et al. |

(Continued)

FOREIGN PATENT DOCUMENTS

| | | |
|---|---|---|
| EP | 2272559 | 1/2011 |
| JP | 2003-526479 | 9/2003 |
| JP | 2009-506253 | 2/2009 |

(Continued)

OTHER PUBLICATIONS

O. Otim, "Optimizing the Kinetics of Persulfate-Mediated Oxidative Coupling of Phenols to 4-Aminoantipyrine," International Journal of Chemical Kinetics, vol. 33, No. 10, pp. 600-604, Aug. 30, 2001. (Year: 2001).*

(Continued)

*Primary Examiner* — Nathan R Price
*Assistant Examiner* — Justin L Zamory
(74) *Attorney, Agent, or Firm* — Dickinson Wright PLLC

(57) ABSTRACT

An infusion set or patch pump is provided for delivering a pharmaceutical agent, such as insulin, to a patient. The infusion set or patch pump has a recessed portion in the bottom face containing a hydrogel and a reactant capable of producing a color change upon contact with the pharmaceutical agent. The reactant includes a mixture of potassium persulfate and 4-aminoantipyrine and optionally horseradish peroxidase, and produces a rapid visually detectable color change when contacted with phenol and/or m-cresol contained in insulin as stabilizing agents.

19 Claims, 4 Drawing Sheets

(56) References Cited

U.S. PATENT DOCUMENTS

2012/0215163 A1    8/2012    Hanson et al.

FOREIGN PATENT DOCUMENTS

| JP | 2012-521822 | 9/2012 |
|----|----|----|
| WO | 01/68163 | 9/2001 |
| WO | 2001068163 A2 | 9/2001 |
| WO | 03/022910 | 3/2003 |
| WO | 2007/023315 | 3/2007 |

OTHER PUBLICATIONS

Canadian Office Action dated May 7, 2019, which issued in the corresponding Canadian Application No. 2,829,129.
Japanese Office Action dated Mar. 27, 2018, which issued in the corresponding Japanese Application No. 2013-211891, including English Translation.
Schoonen, J.W. et al., Determination of polyphenols in wines by reaction with 4-aminoantipyrine and photometric flow-injection analysis, Analytical and Bioanalytical Chemistry, vol. 372, No. 7-8, Apr. 1, 2002 (Apr. 1, 2002), pp. 822-828.
Extended European Search Report, dated Jan. 20, 2014, for EP Patent Application No. 13187549.
Japanese Communication dated Jul. 4, 2017, which issued in the corresponding Japanese Application No. 2013-211891.

* cited by examiner

INFUSION SITE LEAK DETECTION DEVICE

CROSS REFERENCE TO RELATED APPLICATION

This application is a divisional application of U.S. patent application Ser. No. 14/045,261, filed Oct. 3, 2013, now U.S. Pat. No. 9,750,876, which claims the benefit of U.S. Provisional Patent Application No. 61/711,285, filed Oct. 9, 2012, the entire contents of which are incorporated herein by reference.

FIELD OF THE INVENTION

The present invention is directed to a drug delivery device having a leak detector. The present invention is particularly directed to an insulin infusion set that exhibits a visual color change in response to leakage at an infusion site.

BACKGROUND OF THE INVENTION

For patients with diabetes, there are two principal modes of daily insulin therapy. The first mode includes syringes and insulin pens. These devices are simple to use and are relatively low in cost, but they require a needle stick at each injection, typically three to four times per day. The second mode includes insulin infusion therapy, which utilizes an insulin pump. Infusion pumps, although more complex and expensive than syringes and pens, offer the advantages of continuous infusion of insulin via an infusion cannula, precision dosing, and programmable delivery schedules.

The use of an infusion pump requires the use of a disposable component, typically referred to as an infusion set, line set, extension set or pump set, which conveys the insulin from a reservoir within the pump into the skin of the user. An infusion set typically consists of a pump connector, a length of tubing, and a hub or base from which an infusion cannula (i.e., an infusion needle or a flexible catheter) extends. The hub or base has an adhesive which retains the base on the skin surface during use, and which may be applied to the skin manually or with the aid of a manual or automatic insertion device. In most cases, a detachable fluid connector is provided to allow the pump tubing to be disconnected from the hub or base of the infusion set when the user wishes to shower, bathe or swim.

A second way of providing insulin infusion therapy is by means of a patch pump. A patch pump is a self-contained device incorporating an insulin reservoir, pump and cannula in a single housing that can be adhered to the user's skin. A patch pump offers the advantage of not requiring the user to disconnect pump tubing when the user wishes to shower, bathe or swim.

A problem with infusion sets and patch pumps occurs when the cannula separates from the skin of the patient or becomes dislodged such that leakage occurs at the infusion site. Infusion pumps generally dispense insulin in small volumes for long periods of time. When leakage occurs, it is often not noticed by the patient for an extended length of time, resulting in an improper dosage.

Accordingly, there is a continuing need in the industry for improved infusion sets and patch pumps that provide adequate leak detection to the patient.

SUMMARY OF THE INVENTION

The present invention is directed to a drug delivery system having a leak detection system. The invention is particularly directed to an insulin infusion device having a leak detection device for detecting leaks at an infusion site.

Accordingly, one object of the present invention is to provide a fluid delivery device, an insulin delivery device, an infusion set, patch pump or other delivery device having a leak detection component for providing a signal to the patient that leakage at the infusion site has occurred.

Another feature of the invention is to provide an insulin delivery device such as an infusion set, patch pump or other delivery device that provides the patient with a visible indicator that leakage has occurred at an infusion site. The visible indicator in one embodiment is based on a color change of the device, component or material at the infusion site.

An infusion set or patch pump in an embodiment of the invention includes a cannula for penetrating the skin of a patient for delivering a drug or other pharmaceutical agent. A leak detector is provided around the cannula which undergoes a color change as a result of a chemical reaction with one or more compounds in the drug or pharmaceutical agent with a compound on or associated with the leak detector. The leak detector contains chemical compounds that undergo a rapid color change compared to the prior devices when in contact with the drug or pharmaceutical agent.

The fluid or insulin delivery device such as an infusion set or patch pump in an embodiment of the present invention has a base with a bottom face for attaching to the skin of the patient. A center portion of the base has a recessed area and a cannula extending from the base through the recessed area so that the recessed area surrounds the infusion site when attached to the patient. A leak detector capable of undergoing a chemical change when contacted with a drug or pharmaceutical agent is provided in the recessed area. In one embodiment, the leak detector surrounds the cannula and is spaced from the cannula a distance to define a cavity for capturing and retaining the drug or pharmaceutical agent leaking from the infusion site. The infusion set or patch pump includes a clear, transparent portion or window to visualize the color change occurring in the leak detector at the infusion site.

The leak detector in an embodiment of the invention is a hydrogel having at least one reactant contained therein capable of reacting with a compound of the drug or pharmaceutical agent to produce a visible color change. The hydrogel can be attached to the base of the infusion set or patch pump around the cannula. In a preferred embodiment, the hydrogel includes an adhesive layer for attaching the hydrogel in the recessed area of the infusion set around the cannula.

The chemical compounds of the leak detector are capable of producing a color change when contacted by one or more compounds contained in the drug or pharmaceutical, such as a stabilizing agent. In one preferred embodiment, the drug is insulin containing phenolic stabilizing agents such as phenol and m-cresol. The reactive compounds in the leak detector are potassium persulfate and 4-aminoantipyrine, which react with the phenol and m-cresol. Optionally, horseradish peroxidase or other enzyme is added to produce a rapid color change.

The various advantages and features of the invention are attained by providing a fluid delivery device for introducing a fluid to a patient comprising a fluid supply containing an active compound and at least one stabilizing compound. A delivery element is adapted for penetrating the skin of the patient and delivering the fluid to the patient. The delivery device in one embodiment has a leak detector that includes potassium persulfate and 4-aminoantipyrine in an amount sufficient to produce a visible color change when in contact with stabilizing compounds in the fluid.

The features of the invention are further attained in one embodiment by providing an insulin delivery device comprising an insulin supply source containing insulin and at least one phenolic stabilizing compound. An infusion set is adapted for penetrating the skin of a patient and having an interface for contacting skin of the patient. The interface region has a leak detector that includes potassium persulfate and 4-aminoantipyrine in an amount effective to produce a visible color change when contacted with the stabilizing compound.

The features of the invention are also attained by providing an insulin delivery device comprising an insulin supply source containing insulin and an infusion set coupled to the supply source and adapted for penetrating skin of a patient. The infusion set in one embodiment has a base with an interface for attaching to skin of a patient, a cavity formed in the interface, a cannula in the cavity, and a leakage detector within the cavity and surrounding the cannula. The leakage detector has at least one reactant capable of undergoing a color change upon contact with at least one compound in the insulin and is visible through the base.

The additional features of the invention are attained by providing a method of detecting a leak between an insulin infusion set and a point of delivery to a patient. The method comprises providing a leak detector at the point of delivery. The leak detector in one embodiment includes a mixture of potassium sulfate and 4-aminoantipyrine in an amount sufficient to produce a color change upon contact with a phenolic preservative in insulin leaking from the point of delivery.

These and other advantages and salient features of the invention will become apparent from the annexed drawings and the following detailed description of the invention which disclose various embodiments of the present invention.

BRIEF DESCRIPTION OF THE DRAWINGS

The following is a brief description of the drawings, in which.

DETAILED DESCRIPTION OF THE INVENTION

Figure 1:
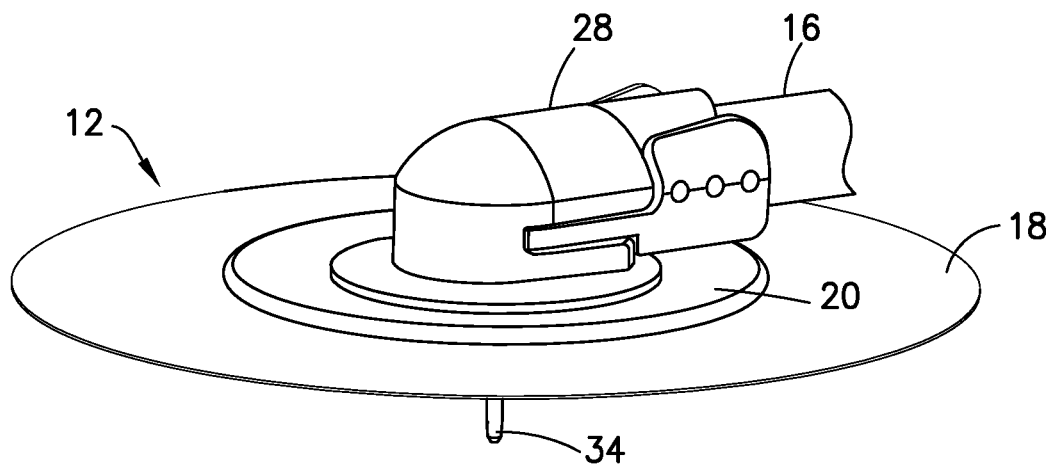
FIG. 1 is a perspective view of an insulin infusion set in one embodiment of the invention.
Figure 2:
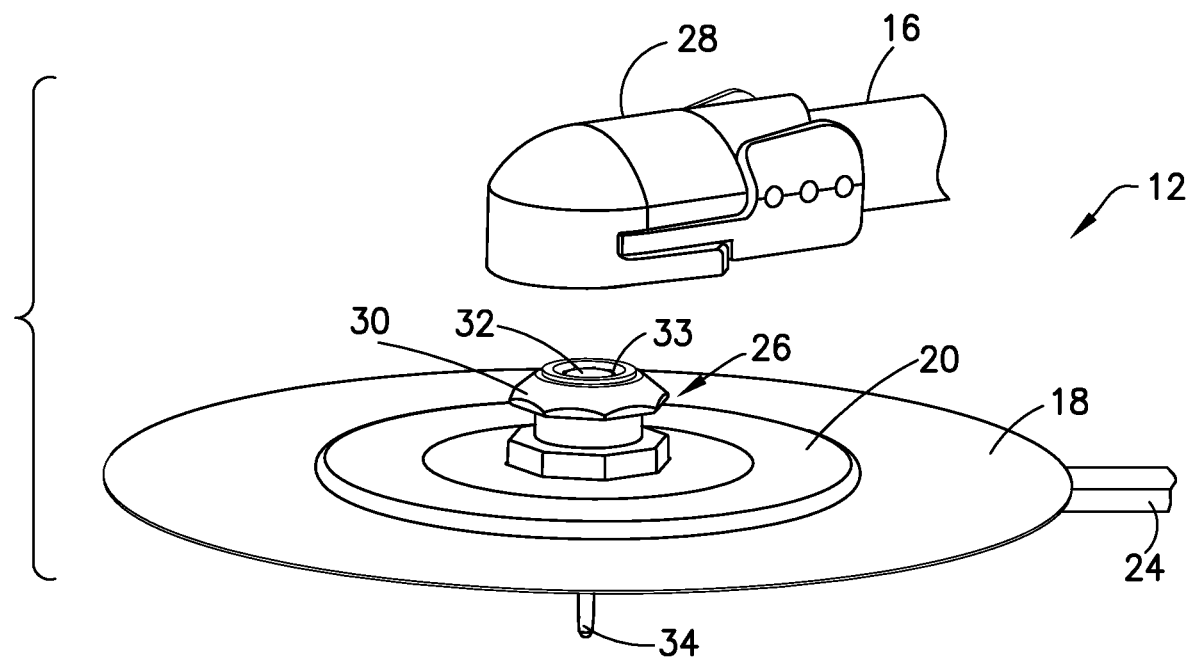
FIG. 2 is an exploded view of the infusion set of FIG. 1 showing the supply coupling being disconnected.

The present invention is directed to a drug delivery device having a leak detection system such as a fluid delivery device or an insulin delivery device. The invention is particularly directed to a fluid or insulin delivery device having a leak detector that provides a visual indication of leakage at the delivery site. The invention is further directed to a fluid delivery device for delivering a fluid containing an active agent to a patient. The fluid delivery device is typically a drug delivery device for delivering a drug such as insulin.

The drug delivery device of the present invention is typically an insulin delivery device such as an insulin infusion set for connecting to an infusion pump as known in the industry. Alternatively, although not shown in the drawings, it may be a self-contained patch pump having an internal drug reservoir. The drug delivery device in the illustrated embodiment of the invention includes a fluid supply shown as an infusion set 12 connected to an infusion pump 14 by a conduit or supply tube 16. The infusion set is primarily for the delivery of insulin to a patient at a controlled rate and dosage. However, other fluids can also be administered by infusion to the patient such as HIV drugs, drugs to treat pulmonary hypertension, pain medications, anti-cancer treatments, vitamins, growth hormones, or other substances.

The delivery device of the invention typically includes an infusion set or other cutaneous or subcutaneous delivery member. The delivery device has a chamber for capturing fluids leaking at the delivery site and producing a visible color change. The fluid delivery device for introducing a fluid to a patient includes a fluid supply for delivering a fluid containing an active agent and a stabilizing or preserving agent, a delivery element for penetrating the skin and a leak detector.

Referring to FIGS. 1-4 of the drawings, the infusion set 12 has a flexible base 18 and a centrally located hub 20. The base 18 is made of a sufficiently flexible material to conform to the patient's skin when attached. The bottom face of the base 18 includes an adhesive 22 for attaching the base to the patient. A protective peel layer 24 is provided to cover the adhesive 22 during storage and which can be removed by the patient at the time of use.

Figure 3:
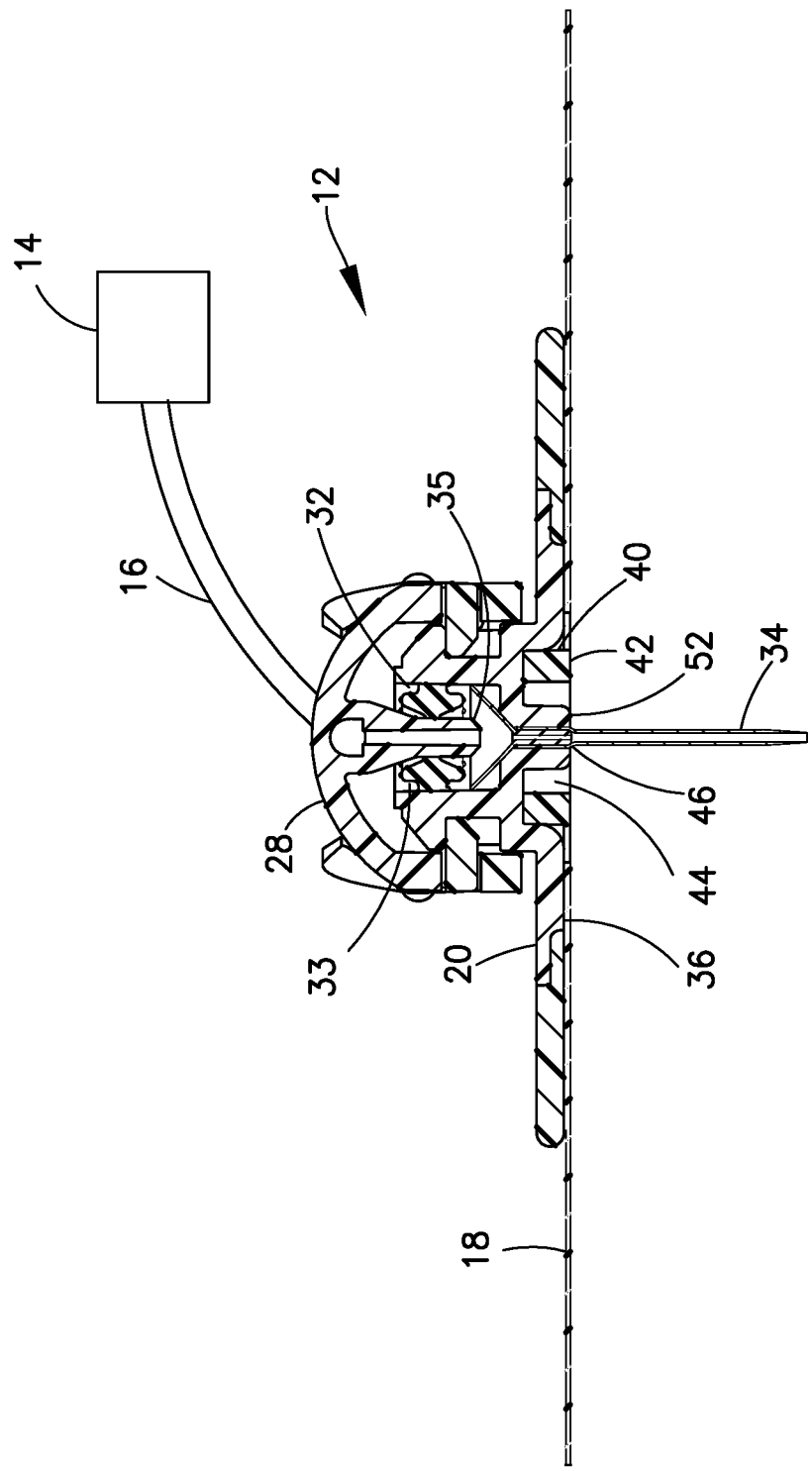
FIG. 3 is a cross-sectional view of the infusion set showing leak detector according to an embodiment of the invention.

The central hub 20 is attached to the base to provide a substantially fluid-tight seal therebetween. The central hub 20 has a top face with a fluid port 26 for connecting to a detachable fluid coupling 28. Preferably, hub 20 is made from a clear and transparent plastic material. Port 26 has a substantially cylindrical configuration with an outwardly extending annular flange 30. The annular flange 30 connects to a corresponding recess in the coupling 28 as shown in FIG. 3. An axial passage 32 sealed near its upper end by a pre-slit resilient septum 33 extends through the port 26 and hub 20 for supplying the fluid to the patient. A blunt plastic cannula 35 within the fluid connector 28 penetrates the septum 33 to establish fluid flow to the infusion set 12.

A cannula 34 or other delivery element for penetrating the skin is coupled to the hub 20 and extends from an interface region on a bottom face 36 of the hub 20 as shown in FIG. 3. The cannula 34 can be a rigid cannula made of stainless steel or a soft flexible cannula as known in the art. The soft flexible cannula typically includes an insertion needle (not shown) that is able to penetrate the skin to position the flexible cannula into the skin after which the insertion needle is removed. Typically, the infusion set will have a flexible cannula and an insertion needle as known in the art.

Figure 4:
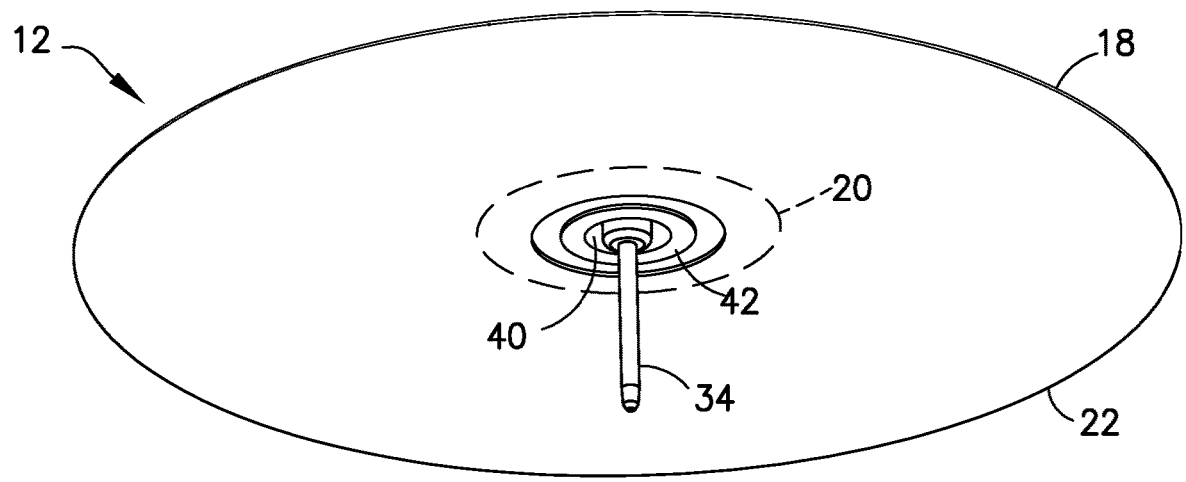
FIG. 4 is a bottom perspective view of the infusion set showing the leak detector.

The bottom face 36 of the hub 20 as shown in FIG. 3 includes an annular recess 40 surrounding a cylindrical cannula support hub 52 and the cannula 34 for forming a cavity in the bottom face of the hub 20. Positioned within the recess 40 is a leak indicator 42. As shown in FIGS. 3 and 4, the leak indicator 42 has an annular shape surrounding the cannula 34 and cannula support 52 to form an open area to capture the infusion liquid. In the embodiment shown, the leak indicator 42 has an annular shape to define an annular cavity 44 surrounding the cannula 34 within the recess 40. As shown, annular cavity 44 is formed between the inner wall of hub 20 and the outer surface of cannula support hub 52. The leak detector is spaced from the cannula a distance to define an open area to capture the infusion liquid. Preferably, the leak detector 42 has a height corresponding to the depth of the recess 40 as shown in FIG. 3. In alternative embodiments, the leak detector 42 can fill the entire recess 40 so that no gap or space is present between the cannula 34 and the leak detector 42. In another embodiment, the leak detector 42 can include an inwardly extending portion that extends between the outer wall and inner wall of annular recess 40 with the cavity 44 being formed below leak detector 42 so that the cavity 44 surrounds the cannula hub 52 and the cannula 34. Preferably, the leak detector extends to the bottom face 36 of the hub 20 to contact the skin of the patient around the cannula 34. In this manner, any fluid leaking at the infusion site 46 is captured by the leak detector 42. The recess 44 is generally preferred to alleviate skin tensioning during insertion of the cannula 34. In other embodiments, the leak detector 42 occupies only a portion of the cavity 44, can be formed from segments or can be a plurality of leak detectors that are contiguous or spaced-apart.

The leak indicator in an embodiment of the present invention is an absorbent material containing a color-changing component that is able to provide a visual color indicator in the event of leakage at the infusion site. The leak detector and the color change is visible by the user through the transparent portions of the hub 20. As shown in FIG. 3, the infusion site 46 at the cannula penetration site is typically where leakage occurs. The leakage can be the result of an improperly inserted cannula or a cannula that has been partially or completely removed as a result of movement of the infusion set 12. In preferred embodiments of the invention, the leak indicator 42 is positioned to provide a rapid visual indicator to the patient that leakage has occurred, thereby providing an opportunity to correct the leakage and provide the intended dosage. The leak detector 42 provides a visual color indicator of leakage through the delivery device.

Referring to FIG. 3, leakage occurring at the infusion site 46 is captured in the cavity 44 and leak detector 42. The fluid being delivered to the patient is absorbed by the leak detector 42. The fluid being delivered is absorbed by the leak detector which then reacts with compounds in the leak detector to provide a visual indicator through the delivery device. In one preferred embodiment, the hub 20 is made of a clear or transparent material so that the color change in the leak detector can be viewed by the patient through the top and/or sides of the hub 20. In further embodiments of the invention, the fluid coupling 28 can also be clear or transparent so that color change can be observed by the patient.

In a preferred embodiment of the invention, the leak detector 42 is made from a transparent high diffusion hydrogel having at least one compound dispersed therein that is capable of undergoing a color change when contacted with the infusion liquid. The hydrogel is preferably formed as a film or cylindrical shaped member having an adhesive backing on one side for attaching the hydrogel to one or more surfaces of a recess in the bottom of an infusion set. Examples of hydrogels include polyacrylamides, silicone hydrogels, crosslinked polyethylene oxide and crosslinked polyvinylpyrrolidone. The clear or transparent components of the infusion set enable visualization of the reaction by a color change through one or more parts of the infusion set.

Figure 5:
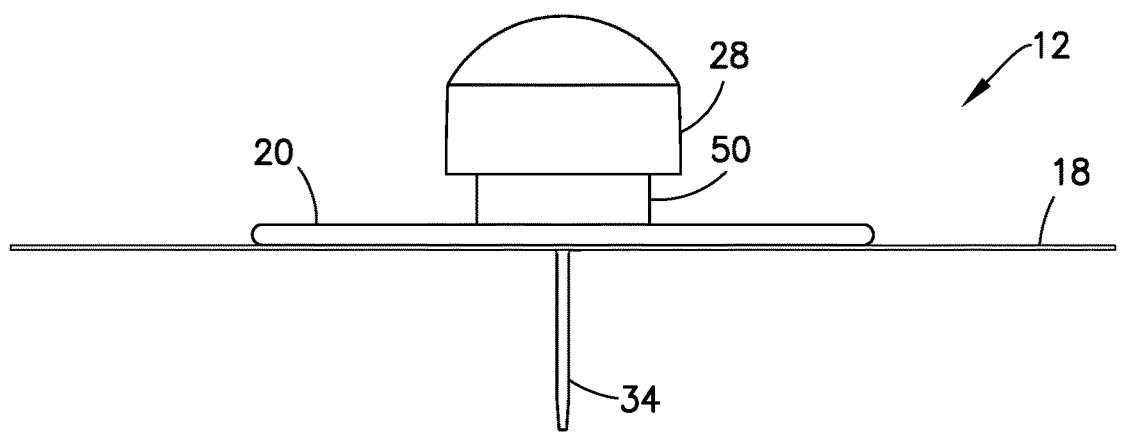
FIG. 5 is a side view of the infusion set in a second embodiment of the invention.
Figure 6:
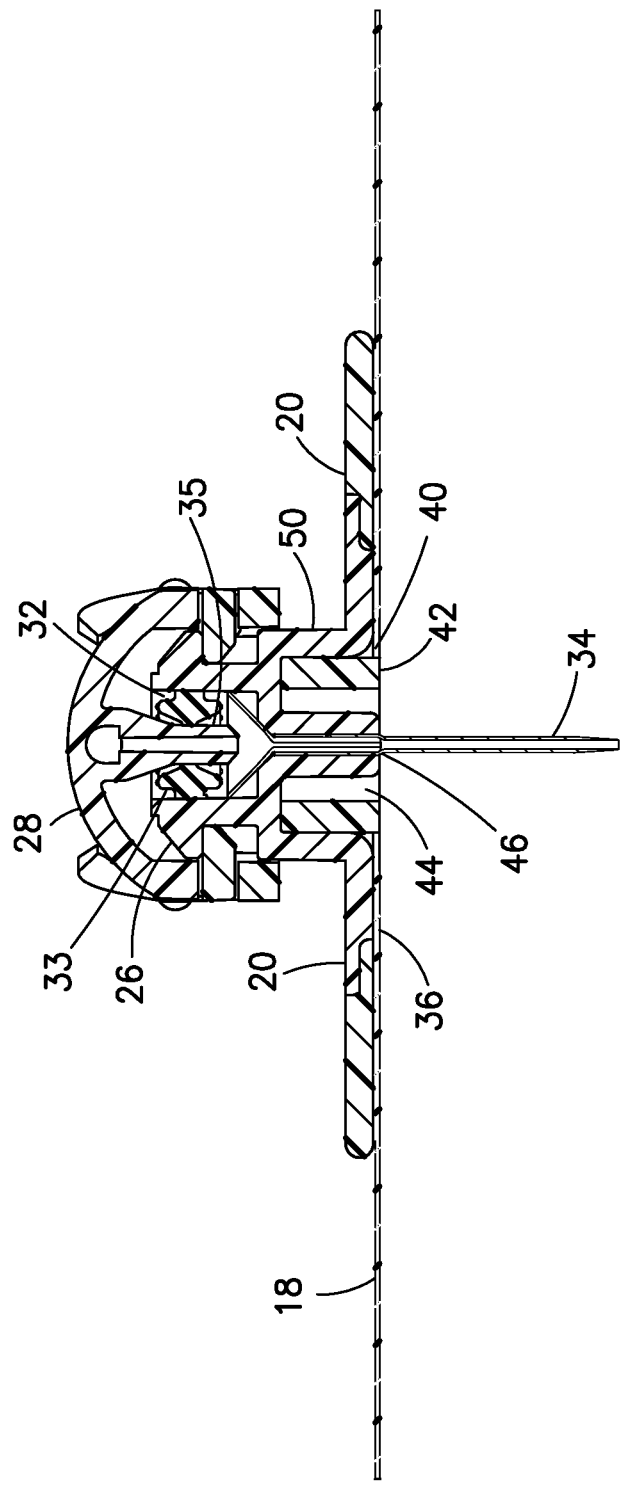
FIG. 6 is a cross-sectional view of the infusion set of FIG. 5.

In one embodiment of the invention, the leak indicator is formed within a portion of the hub 20 that has a cylindrical shape. In the embodiment shown in FIGS. 5 and 6, the leak detector 40 is provided within the cylindrical portion 50 of the port 26. The leak detector 40 is visible through the side wall of the cylindrical portion 50 of the port 26 as well as the top face of the hub 20 to enhance visualization when a color change occurs. In the embodiment of FIGS. 5 and 6, the leak detector 42 has a cylindrical shape to extend from the bottom face of the hub upwardly along the cylindrical portion 50. The cannula 34 is connected to the port 26 as shown.

In one embodiment of the invention, the infusion liquid is an insulin formulation. The leak detector contains at least one component that reacts with a component or compound of the insulin formulation that is not present in body fluids to avoid giving a false indication of leakage of the insulin formulation. Insulin formulations typically include insulin, hexamer zinc stabilizer preservatives, pH buffers, surfactants such as glycerol and tonicity agents such as NaCl. Common insulin preservatives or stabilizing agents include m-cresol, phenol, and mixtures thereof.

In one preferred embodiment of the invention, the leak detector 42 includes one or more compounds that react with the stabilizing agents, namely m-cresol and/or phenol, to produce a visual color change when the infusion liquid is absorbed by the leak detector. The color changing compounds in the leak detector are preferably clear or opaque initially and produce a color change when reacted with the stabilizing agents of the insulin or other infusion liquid.

The color changing compounds of an embodiment of the invention include a mixture of 4-aminoantipyrine and an oxidizing agent in an effective amount to produce a color change by reacting with the stabilizing agents when the infusion liquid contacts the leak detector 42. The preferred oxidizing agent is potassium persulfate, $K_2S_2O_8$. The mixture of 4-aminoantipyrine and potassium persulfate reacts with the m-cresol and/or phenol in the insulin formulation to transform the leak detector from a clear hydrogel to a dark blue color that is visible through the transparent hub 20. Potassium persulfate is a preferred oxidizing agent and has been found to provide a rapid color change in the presence of phenol, m-cresol and 4-aminoantipyrine compared to other oxidizing agents. For example, it has been found that potassium persulfate provides a faster color change compared to potassium ferricyanide. The m-cresol and/or phenol react with potassium persulfate and 4-aminoantipyrine to produce quinoneimine having a dark blue color that is visible through the hub 20.

In further embodiments, the hydrogel can also include a catalyst or enzyme to enhance the speed of the reaction and amplify the color change. In one embodiment, horseradish peroxidase (HRP) is included in the hydrogel matrix in combination with the 4-aminoantipyrine and potassium persulfate. A deep blue complex is formed during the reaction with m-cresol and phenol. Horseradish peroxidase functions as a catalyst to create an enzymatic amplification of the reaction and the blue complex formed by the reaction. The presence of the horseradish peroxidase enables rapid detection of small amounts of insulin to enable patients to observe the leakage reliably and quickly after the leakage starts.

The amount of the various compounds and components are preferably present in an amount effective to provide a prompt and reliable reaction time for the detection of the leakage of insulin from an infusion site. The pH of the hydrogel is also adjusted to maximize the reaction. The hydrogel can also contain a contrasting color from the blue reaction product to enhance the visualization of the color change. For example, the hydrogel can have a white or cream colored pigment that will enhance the color change.

While various embodiments have been selected to illustrate the invention, it will be understood that various changes and modifications can be made without departing from the scope of the invention as defined in the appended claims and their equivalents.

What is claimed is:

1. A method of delivering a fluid to a patient by a fluid delivery device and detecting leakage from an injection site in the patient, said method comprising;
    providing a delivery device having a base with a bottom face having an adhesive, a hub coupled to the base and having a bottom face, a cavity formed in said hub and recessed with respect to said bottom face of said hub and said base, a cannula configured for being inserted into the skin of the patient and oriented within said cavity of said hub, and a fluid supply connected to said hub for delivering the fluid containing an active agent and at least one stabilizing agent, and a leak detector positioned in said cavity of said hub and surrounding said cannula and spaced inwardly from said adhesive and said base, said leak detector comprising potassium persulfate and 4-amino-antipyrine;
    introducing said catheter into the injection site on the skin of the patient and attaching said base to the skin of the patient by the adhesive and forming a fluid seal around the hub and around the cavity;
    introducing said fluid through said cannula into the patient at the injection site and capturing fluid leakage from said injection site in said cavity of the hub where said stabilizing agent in said fluid from said injection site reacts with said leak detector to produce a visible color change that is visible through said hub when leakage occurs.

2. The method of claim 1, wherein
said leak detector comprises a hydrogel impregnated with said potassium persulfate and 4-aminoantipyrine.

3. The method of claim 2, wherein
said hydrogel is attached to said hub by an adhesive surrounding said catheter.

4. The method of claim 1, wherein
said catheter is a soft, flexible catheter, and said method comprising introducing said soft, flexible catheter into said patient by an introducer needle.

5. The method of claim 2, wherein
said hydrogel surrounds said cannula and is spaced outwardly from said cannula.

6. The method of claim 1, wherein
said hub of said delivery device has a top face with at least one substantially transparent portion to visualize the color change through said at least one substantially transparent portion of said hub, the hub having a cannula support and a side wall surrounding the cannula support and defining the cavity between the side wall of the hub and the cannula support for receiving said leak detector, and visualizing the color change through the side wall of the hub.

7. The method of claim 1, wherein
said active agent comprises insulin and said at least one stabilizing agent is selected from the group consisting of m-cresol, phenol, and mixtures thereof.

8. The method of claim 2, wherein
said hydrogel further comprises an effective amount of horseradish peroxidase to catalyze the reaction.

9. A method of delivering insulin to an injection site of a patient and detecting leakage from said injection site, said method comprising:
    providing a delivery device having an insulin supply source for delivering a fluid containing insulin and at least one phenolic stabilizing agent to the patient, and an infusion set having a base, a hub having a cavity, and a contact area having an adhesive for contacting skin of the patient and surrounding said cavity, a cannula in said cavity, said cavity surrounding said cannula and configured for capturing insulin leakage in said cavity from said cannula at an infusion site, a leak detector positioned in the cavity of said hub and surrounding the cannula, said leak detector including potassium persulfate and 4-amino-antipyrine in an amount effective to produce a visible color change when contacted with the stabilizing agent of said insulin, the leak detector positioned in the cavity of said base between the contact area and the cannula, and spaced outwardly from said cannula to define an annular open area around said cannula;
    introducing said catheter into the injection site in the skin of the patient and attaching said base to said skin of the patient by the adhesive to surround said injection site, cavity, and cannula; and
    introducing said insulin through said cannula into the patient at the injection site and capturing insulin leakage from said injection site in said cavity and said open area where said phenolic stabilizing agent leaking from said injection site contacts said leak detector in said cavity of said hub to produce a visible color change that is visible through said hub when leakage occurs.

10. The method of claim 9, wherein
said at least one stabilizing agent is selected from the group consisting of m-cresol, phenol, and mixtures thereof.

11. The method of claim 9, wherein
said leak detector further comprises an effective amount of horseradish peroxidase to catalyze the reaction between the potassium persulfate, 4-aminoantipyrine and the stabilizing agent.

12. The method of claim 9, wherein
said leak detector is positioned in said cavity of said hub around said cannula and spaced inwardly from said adhesive.

13. The method of claim 12, wherein
said leak detector further includes a hydrogel containing said potassium sulfate and 4-aminoantipyrine.

14. The method of claim 13, wherein
said hydrogel is attached to said interface by an adhesive.

15. The method of claim 13, wherein
said interface includes a contact area surrounding said cavity, said contact area having said adhesive, and said method comprising attaching said contact area to the skin of the patient by said adhesive and containing said insulin leakage within said cavity.

16. The method of claim 14, wherein said leak detector is spaced inwardly from said adhesive and spaced outwardly from said cannula.

17. The method of claim 9, wherein said cannula is a soft flexible cannula, and where said soft flexible cannula is introduced into the patient by an insertion needle.

18. A method of detecting a leak between an insulin infusion set and an injection site of a patient, said method comprising:
    providing the infusion set having an interface with a base having an adhesive for attaching directly to skin of a patient, a hub coupled to said base and having a side wall, a cavity formed in the hub and recessed with respect to a bottom side of said based and with respect to a bottom side of said hub, and a cannula positioned in said cavity and extending from said base a distance to penetrate the skin of the patient, a leak detector positioned in said cavity of said hub between said adhesive and said cannula and surrounding said cannula and spaced outwardly from said cannula a distance to define the cavity, said leak detector spaced inwardly from said base and said adhesive and including a mixture of potassium sulfate and 4-aminoantipyrine, and said base having a bottom face with an adhesive for attaching to the skin of the patient and surrounding said cavity, leak detector and cannula and where said cavity is formed between said side wall of said hub and said cannula;

attaching said base to the skin and inserting the cannula into the skin of the patient, introducing insulin through said cannula into said patient at said injection site, and capturing insulin leakage in said cavity at the injection site where said insulin contacts said leak detector to produce a color change that is visible through said interface.

19. The method of claim 18, wherein said leak detector further comprises horseradish peroxidase.

* * * * *